US00PP34203P2

(12) United States Plant Patent
Heuger

(10) Patent No.: US PP34,203 P2
(45) Date of Patent: May 3, 2022

(54) ***HELLEBORUS* PLANT NAMED 'COSEH 5800'**

(50) Latin Name: ***Helleborus niger* X *Helleborus* x *hybridus***
Varietal Denomination: COSEH 5800

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 17/514,306

(22) Filed: Oct. 29, 2021

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'COSEH 5800', characterized by its upright to slightly outwardly spreading and mounded plant habit; moderately vigorous growth habit; dark green-colored leaves; freely flowering habit; large purplish red to reddish purple-colored flowers; and good garden performance.

1 Drawing Sheet

Figure 2:
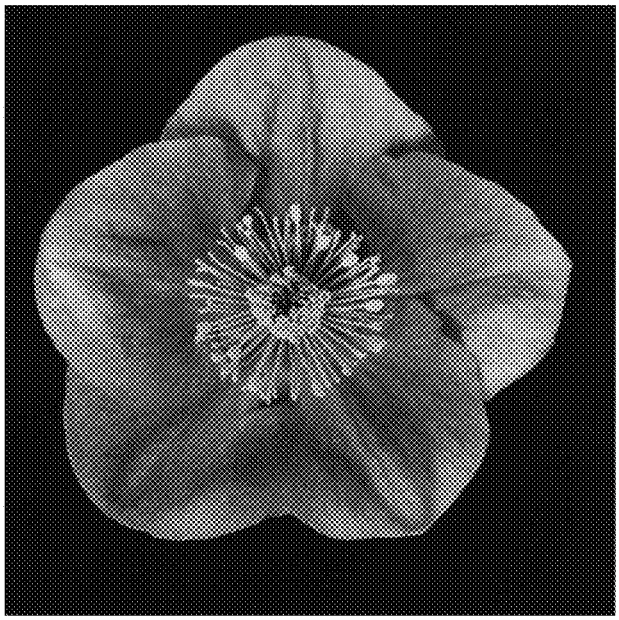

Botanical designation: *Helleborus niger* X *Helleborus* x *hybridus*.

Cultivar denomination: 'COSEH 5800'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Nov. 30, 2020, application number 2020/3088. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 5800'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in January, 2012 of a proprietary selection of *Helleborus niger* identified as code number P780, not patented, as the female, or seed, parent and an unnamed selection of *Helleborus* x *hybridus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2013.

Asexual reproduction of the new *Helleborus* plant by in vitro axillary meristem culture in a controlled environment in Glandorf, Germany since April, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 5800'. These characteristics in combination distinguish 'COSEH 5800' as a new and distinct *Helleborus* plant:

1. Upright to slightly outwardly spreading and mounded plant habit.
2. Moderately vigorous growth habit.
3. Dark green-colored leaves.
4. Freely flowering habit.
5. Large purplish red to reddish purple-colored flowers.
6. Good garden performance.

Plants of the new *Helleborus* differ from plants of the female parent selection in the following characteristics:

1. Leaves of plants of the new *Helleborus* are lighter green in color than leaves of plants of the female parent selection.
2. Flowers of plants of the new *Helleborus* are purplish red to reddish purple in color whereas flowers of plants of the female parent selection are white in color.

Plants of the new *Helleborus* differ from plants of the male parent selection in the following characteristics:

1. Leaf margins of plants of the new *Helleborus* are not as deeply serrate as leaf margins of plants of the male parent selection.
2. Flowers of plants of the new *Helleborus* are purplish red to reddish purple in color whereas flowers of plants of the male parent selection are reddish in color.

Plants of the new *Helleborus* can also be compared to plants of *Helleborus niger* X *Helleborus* x *hybridus* 'LEM 100', disclosed in U.S. Plant Pat. No. 25,646. In side-by-side comparisons, plants of the new *Helleborus* differ primarily from plants of 'LEM 100' in plant and growth habit as plants of the new *Helleborus* are more vigorous than and not as compact as plants of 'LEM 100'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

Figure 1:
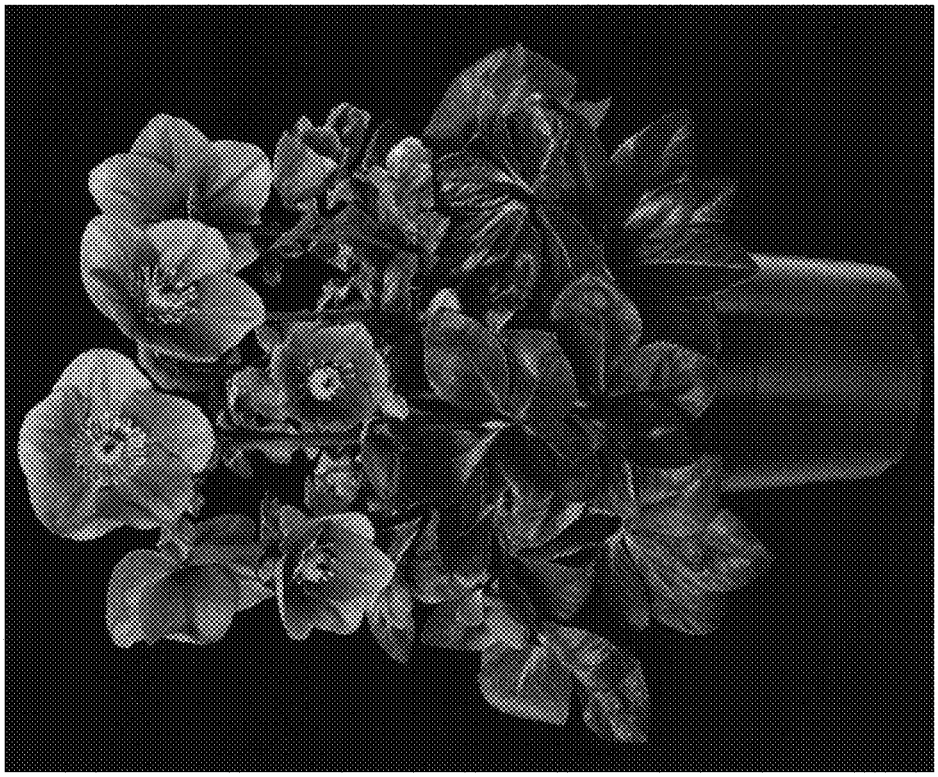

The photograph on the left side of the photographic sheet (FIG. 1) is a side perspective view of a typical flowering plant of 'COSEH 5800' grown in a container.

The photograph on the right side of the photographic sheet (FIG. 2) is a close-up view of a typical flower of 'COSEH 5800'.

DETAILED BOTANICAL DESCRIPTION

The aforementioned photographs and following observations, measurements and values describe plants grown during late autumn and winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were eleven months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 5800'.

Parentage:

*Female, or seed, parent*.—Proprietary selection of *Helleborus niger* identified as code number P780, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to slightly outwardly spreading and mounding plant habit with flowers held above the foliar plane; plant shape, roughly flattened globular; moderately vigorous growth habit and moderate growth rate.

*Plant height, soil level to top of foliar plane*.—About 17.4 cm.

*Plant height, soil level to top of flowers*.—About 47.7 cm.

*Plant diameter* (*area of spread*).—About 34.5 cm.

Leaf description:

*Arrangement*.—Leaves arranged in basal rosettes; leaves palmately compound with typically five leaflets per leaf.

*Leaf length*.—About 17.9 cm.

*Leaf width*.—About 20.6 cm.

*Leaflet length*.—About 11 cm.

*Leaflet width*.—About 7.3 cm.

*Leaf shape*.—Palmate; roughly reniform in outline.

*Leaflet shape*.—Elliptic to obovate.

*Leaflet apex*.—Acute.

*Leaflet base*.—Attenuate.

*Leaflet margin*.—Serrate; younger leaves slightly undulate; older leaves coarsely undulate.

*Leaflet texture and luster, upper and lower surfaces*.—Smooth, glabrous; coriaceous; moderately glossy.

*Leaflet venation pattern*.—Pinnate.

*Leaflet color*.—Developing leaflets, upper surface: Close to 137A; midvein tinged at the base with close to N186C. Developing leaflets, lower surface: Close to 146B; venation, close to between N186C and 200B. Fully developed leaflets, upper surface: Darker than between 147A and N189A; venation, close to 144A and 144B and towards the base, close to 200A to 200B. Fully developed leaflets, lower surface: Close to between 146A and 147B; venation, close to 145A.

*Petioles*.—Length: About 13.2 cm. Diameter: About 7 mm to 8 mm. Strength: Strong. Texture and luster, upper and lower surfaces: Smooth, glabrous; slightly glossy. Color, upper and lower surfaces: Close to 144B.

Flower description:

*Flower shape and habit*.—Rotate single flowers; flowers slightly bowl-shaped; flowers arranged in panicles; freely flowering habit numerous flowers developing during the flowering season; flowers face mostly outwardly to slightly nodding.

*Fragrance*.—None detected.

*Natural flowering season*.—Plants begin flowering about ten months after planting; plants flower naturally from early winter into the winter in Germany.

*Flower longevity on the plant*.—About ten days; sepals persistent, other flower parts are not persistent.

*Flower buds*.—Length: About 2.6 cm. Diameter: About 1.4 cm. Shape: Ovate. Texture and luster: Smooth, glabrous; matte. Color: Close to 145C; distally, tinged with N77B; venation, close to 70A.

*Inflorescence height* (*including peduncle*).—About 35.2 cm.

*Inflorescence diameter*.—About 11.8 cm.

*Flower diameter*.—About 9.5 cm by 9.5 cm.

*Flower depth*.—About 2.5 cm.

*Petals*.—All petals are transformed into nectaries.

*Sepals*.—Quantity and arrangement: About five, arranged in a single whorl. Length: About 4.8 cm. Width: About 4.7 cm. Shape: Broadly ovate; flat to slightly concave. Apex: Obtuse to rounded. Base: Broadly cuneate. Margin: Entire; moderately undulate. Texture and luster, upper surface: Smooth, glabrous; matte. Texture and luster, lower surface: Smooth, glabrous; slightly glossy. Color: When opening, upper surface: Close to 70A and 70B; towards the margins and apex, close to 75A. When opening, lower surface: Close to 70B and N75B; towards the apex, close to N75B; venation, close to 71A. Fully opened, upper surface: Close to 70B and 71B, towards the apex and margins, close to 70B and 75A; venation, similar to lamina colors; with subsequent development, color becoming closer to 70A and 70B and towards the apex, slightly tinged with close to 151B to 151C. Fully opened, lower surface: Close to 70B; towards the apex and margins, close to 186C; venation, close to 64A; with subsequent development, color becoming closer to between 70B and N75B, towards the apex, slightly tinged with close to 146D and venation, close to 71A.

*Flower bracts*.—Quantity per flower: Typically one or two at each node in the inflorescence. Length: About 6.5 cm. Width: About 4.9 cm. Shape: Ovate, occasionally with two apical lobes. Apex: Acute to broadly and bluntly acute. Base: Truncate. Margin: Mostly entire, distally, serrate. Color, upper surface: Close to between NN137A and 147A; towards the base, close to 144B. Color, lower surface: Close to 147B.

*Peduncles*.—Length: About 26.5 cm. Diameter: About 9 mm to 10 mm. Aspect: About 25° from vertical. Strength: Strong. Texture and luster: Smooth, glabrous; moderately glossy. Color: Close to 144A, heavily covered with fine dots, close to 183D; higher density of dots towards the base, close to 187A.

*Pedicels*.—Length: About 4 cm. Diameter: About 3 mm. Aspect: About 10° to 22.5° from peduncle axis. Strength: Moderately strong. Texture and luster: Smooth, glabrous; slightly glossy. Color: Close to 150A and 150B; heavily covered with fine dots, close to 183C.

*Reproductive organs*.—Stamens: Quantity per flower: About 80. Filament length: About 1.8 cm. Filament color: Close to 155B. Anther shape: Double and broadly reniform; basifixed. Anther size: About 2 mm by 3 mm. Anther color: Close to 151C and 151D. Pollen amount: Scarce. Pollen color: Whitish. Pistils: Quantity per flower: About seven to ten. Pistil length: About 1 cm. Stigma diameter: About 0.3 mm. Stigma shape: Club-shaped. Stigma color: Close to 150D. Style length: About 9.5 mm. Style color: Close to 187A. Ovary color: Close to 145C; rib, close to 187C. Nectaries (transformed petals): Quantity per flower: About 15. Length: About 1.15 cm. Diameter: About 4 mm. Shape: Tubular, flattened. Texture and luster, inner and outer surfaces: Smooth, glabrous; slightly glossy. Color, immature, inner and outer surfaces: Close to N144D; towards the base, close to 151A. Color, mature, inner and outer surfaces: Distally, close to N144B and proximally, close to 146C to 146D; at the base, close to 151A; venation, similar to lamina colors; with subsequent development, becoming closer to N144B and at the base, close to 151A.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 5800' as illustrated and described.

* * * * *